United States Patent [19]
Swenson et al.

[11] Patent Number: 5,776,057
[45] Date of Patent: *Jul. 7, 1998

[54] VIRTUAL MEDICAL INSTRUMENT FOR PERFORMING MEDICAL DIAGNOSTIC TESTING ON PATIENTS

[75] Inventors: Michael R. Swenson, San Diego; Gregory R. Holland, Irvine, both of Calif.

[73] Assignee: CMeD, Inc., Irvine, Calif.

[*] Notice: The term of this patent shall not extend beyond the expiration date of Pat. No. 5,623,925.

[21] Appl. No.: 794,380

[22] Filed: Feb. 4, 1997

Related U.S. Application Data

[62] Division of Ser. No. 463,055, Jun. 5, 1995, Pat. No. 5,623,925.

[51] Int. Cl.[6] ................................. A61B 5/0205
[52] U.S. Cl. .................... 600/301; 600/483; 600/508
[58] Field of Search .......................... 128/630, 670, 128/709, 903; 600/301, 483, 508

[56] References Cited

U.S. PATENT DOCUMENTS

| | | | |
|---|---|---|---|
| 4,051,522 | 9/1977 | Healey et al. | 128/903 |
| 4,356,475 | 10/1982 | Neumann et al. | 128/709 |
| 4,695,955 | 9/1987 | Faisandier | 128/696 |
| 5,307,263 | 4/1994 | Brown | 128/668 |
| 5,331,594 | 7/1994 | Crawford, Jr. | 364/413.02 |
| 5,623,925 | 4/1997 | Swenson et al. | 128/630 |

*Primary Examiner*—Lee S. Cohen
*Assistant Examiner*—Eric F. Winakur
*Attorney, Agent, or Firm*—Howard R. Lambert

[57] ABSTRACT

A virtual medical instrument (VMI) system comprises data storage for storing input diagnostic test protocols for two or more of EEG, EKG, EMG/NCV, PFT, CMG, EP, ENG, visual acuity, visual field, limb dynometric and audiogram testing. The VMI system includes a universal interface having a number of electrical contacts and sets of electrical conduits associated with the different stored diagnostic test protocols. A selector enables a system user to select any one of the stored diagnostic test protocols for conducting on a patient. The system is constructed to enable the selected diagnostic test protocol to be performed on a patient after the corresponding set of electrical conduits are connected to the universal interface contacts and to the patient. Further included is an electrical signal generator connected to the universal interface for providing electrical signals to the patent if such electric signals are required by the selected test protocol. Electrical signals are received by the system through the electrical conduits connected to the universal interface from a patient and an output corresponding to the received electrical signals is provided, the output including one or more of strip chart printer, conventional printer, modem, computer diskette, audio recorder and video recorder.

3 Claims, 2 Drawing Sheets

5,776,057

VIRTUAL MEDICAL INSTRUMENT FOR PERFORMING MEDICAL DIAGNOSTIC TESTING ON PATIENTS

This application is a division of application Ser. No. 08/463,055, filed Jun. 5, 1995, now U.S. Pat. No. 5,623,925.

BACKGROUND OF THE INVENTION

1. Field of the Invention

The present invention relates generally to the field of medical and medical office electrical apparatus, and, more particularly, to medical office electrical apparatus such as are used for performing various routine medical diagnostic tests, such as EKG (electrocardiogram), EEG (electroencephalogram) and EMG (electromyogram) tests on patients.

2. Background Discussion

As is well known, various different types of routine diagnostic tests, in accordance with specific test protocols, are performed on patients by physicians and other medical professionals in doctors' offices, clinics, hospitals and other medical facilities. Some test protocols involve passive testing in which bioelectrical signals are received for analysis from a patient undergoing testing. Others diagnostic tests involve active testing in which electrical stimuli are applied to a patient undergoing testing and the resulting electrical response signals from the patient are received for analysis.

Exemplary of such medical diagnostic tests are EKG tests which receive patient-generated electrical signals which are indicative of the patient's heart condition, and may be used to detect a heart attack, a cardiac arrhythmia, or as part of a routine physical examination.

Another such familiar medical diagnostic test is the EEG test during which a recording is made of patient-generated electrical signals indicative of the patient's brain activity. EEG tests may, for example, be used to determine the nature and severity of a seizure disorder or to assist a physician diagnosis of the extent of brain damage caused, for example, by a brain tumor or trauma.

Other of such diagnostic testing protocols include, without limitation: electromyographic (EMG) tests in which there are obtained electrical signals or impulses associated with the activity of a patient's skeletal muscles, useful in diagnosing neuromuscular disorders; cystometrographic (CMG) tests useful in the diagnosis of urinary diseases; pulmonary function tests (PFT), useful for determining the physiological reserve of a patient's lungs in the presence of such diseases as pneumonia, lung cancer and emphysema; visual acuity and visual field testing, useful in the diagnosis of ocular diseases; limb dynamometry, useful in diagnosing muscular diseases; nerve conduction velocity, useful in the diagnosis of diseases of the central nervous system; evoked potential (EP), useful in the diagnosis of diseases and localizing lesions of the central nervous system; electrostagmography (ENG), useful in the diagnosis of disorders of the central and peripheral pathways subserving balance; and audiometry, useful in the diagnosis of diseases affecting hearing.

Heretofore, as far as is known to the present inventor, each of such medical diagnostic tests have required the use of a separate, dedicated testing machine or apparatus. Thus, by way of illustration, the performing of EKG tests on patients has heretofore required the use of dedicated EKG machines and the performing of EEG tests on patients has heretofore required the use of dedicated EEG machines.

It can readily be appreciated that this prior requirement of having a particular dedicated testing machine or apparatus for each different medical diagnostic test results in various cost-related problems. Not only does the need to have available different, dedicated medical diagnostic machines for each different medical diagnostic test result in considerable expense to properly equip and maintain a medical office, hospital or clinic, but such need for a number of different dedicated medical diagnostic machines also requires the allocation of usually expensive floor space and adds to the clutter of a medical office.

Importantly, in the present climate of medical cost containment and reduction, especially in the area of medical insurance and federal and state medical (e.g., MEDICARE and MEDICAL) reimbursements for medical procedures, the minimizing of medical office costs, including equipment costs, is now more and more important, if not critical, to the medical profession, not to mention the general public.

For these and other reasons, the present inventor has invented a universal medical diagnostic testing system which is sometimes referred to hereafter as a "virtual medical instrument (VMI) system.

The present virtual medical instrument system enables each of a large number of generally routine medical diagnostic tests protocols to be to be conducted on patients by a single, adaptable system, which is preferably software driven. This new system, thus eliminates the need for a different dedicated diagnostic test machine for each different medical diagnostic test protocol to be performed by medical professionals on patients.

In addition to use in the multi-speciality medical office and the reduction in medical office costs provided by this new VMI system, the system also lends itself well to the efficient equipping of small, mobile medical offices, as may be beneficial in public health services, military clinics, in developing nations and mobile clinics in the event of major catastrophes, such as earthquakes, hurricanes and terrorist activities.

SUMMARY OF THE INVENTION

In accordance with the present invention, a virtual medical instrument system enables the selective performing on patients of one or more of a plurality of different, medical diagnostic tests. The system includes information (data) storage means for storing the plurality of diagnostic test protocols which include at least two, and preferably all of the following diagnostic test protocols: EEG, EKG, EMG/NCV, PFT, CMG, EP, ENG, visual acuity, visual field, limb dynamometry and audiogram.

Included in the system are means for inputting information into the information storage means and a universal interface having a number of electrical contacts. Selecting means are connected to the information storage means for enabling a user of the system to select any one of the plurality of different stored patient diagnostic test protocols for conducting the tests on a patient. Selecting any one of the stored diagnostic test protocols automatically determines and selects a corresponding set of electrical conduits to be connected to particular contacts of the universal interface.

Included in the system are operating means for causing the selected diagnostic test protocol, and only that test protocol, to be performed on a patient after the corresponding set of electrical conduits are connected to the universal interface contacts and to a patient on which the selected diagnostic-test protocol is to be performed.

Further included in the system are means connected for receiving electrical signals through the set of electrical conduits connected to said universal interface contacts from a patient undergoing the selected diagnostic test. Preferably the receiving means include a preamplifier connected to or within the universal interface for amplifying one or more of the electrical signals received from the patient undergoing the selected diagnostic test.

Associated with the receiving means are means for generating and providing a detectable output corresponding to the received electrical signals from the patient undergoing the diagnostic test, the output means including at least one, and preferably more than one, of the following: strip chart printer, conventional printer, modem, computer diskette, audio recorder and video recorder.

In accordance with a preferred embodiment of the invention, and as a safety measure, there are included comparing means associated with the electrical signal receiving means for comparing initially-received electrical signals from a patient undergoing the selected diagnostic test protocol with expected electrical signals associated with the selected diagnostic test protocol and for alerting a user of the system when the initially-received electrical signals are substantially different from the expected electrical signals, thereby alerting the user to the possibility that the set of electrical conduits used for the selected diagnostic test are not properly connected to the universal interface contacts or that there is possibly a system malfunction.

If some of the stored medical diagnostic test protocols require that electrical stimuli be provided to the patient undergoing those test protocols and the electrical signals received from the patient are in response to such electrical stimuli, the virtual medical office system of the present invention includes electrical signal generating means that are connected to the universal interface for providing electrical signals to a patent undergoing the selected diagnostic test protocol in accordance with patient stimuli requirements of the selected test protocol.

Preferably the selecting means include verifying means for assuring that when the electrical conduits associated with the selected diagnostic test protocol are connected to particular ones of the universal interface contacts only the preselected diagnostic test protocol is enabled for performing on a patient.

A visual display, such as a cathode ray tube (CRT), is connected for providing visual information to a user of the system regarding the medical test protocols that can be selected and information concerning the selected medical test protocol. Preferably, the visual display is connected to the signal receiving means for visually displaying electrical signals received from the patient through the universal interface.

The system may include limit setting means associated with the signal receiving means and the selecting means for enabling a user of the system to set upper and/or lower amplitude limits for at least some of the received electrical signals associated with some of the medical diagnostic test protocols and for providing information to the user when the set amplitude limits are exceeded.

The virtual medical instrument system of the present invention thus enables a user or multiple users to perform selected ones of stored medical diagnostic test protocols on patients without the necessity of having a dedicated piece of diagnostic test equipment or machine for each different diagnostic test. Medical office costs are accordingly reduced by the virtual office system's enabling a number of different tests to be performed and office efficiency is increased by just using one system for all the different diagnostic tests.

BRIEF DESCRIPTION OF THE DRAWINGS

The present invention can be more readily understood by a consideration of the following detailed description when taken in conjunction with the accompanying drawings in which:

FIG. 3 is a representative diagram depicting the manner in which a user of the system determines if the system is properly connected for performing the selected medical test on a patient.

In the FIGS. the same elements or features are given the same reference number.

DETAILED DESCRIPTION OF THE INVENTION

Figure 1:
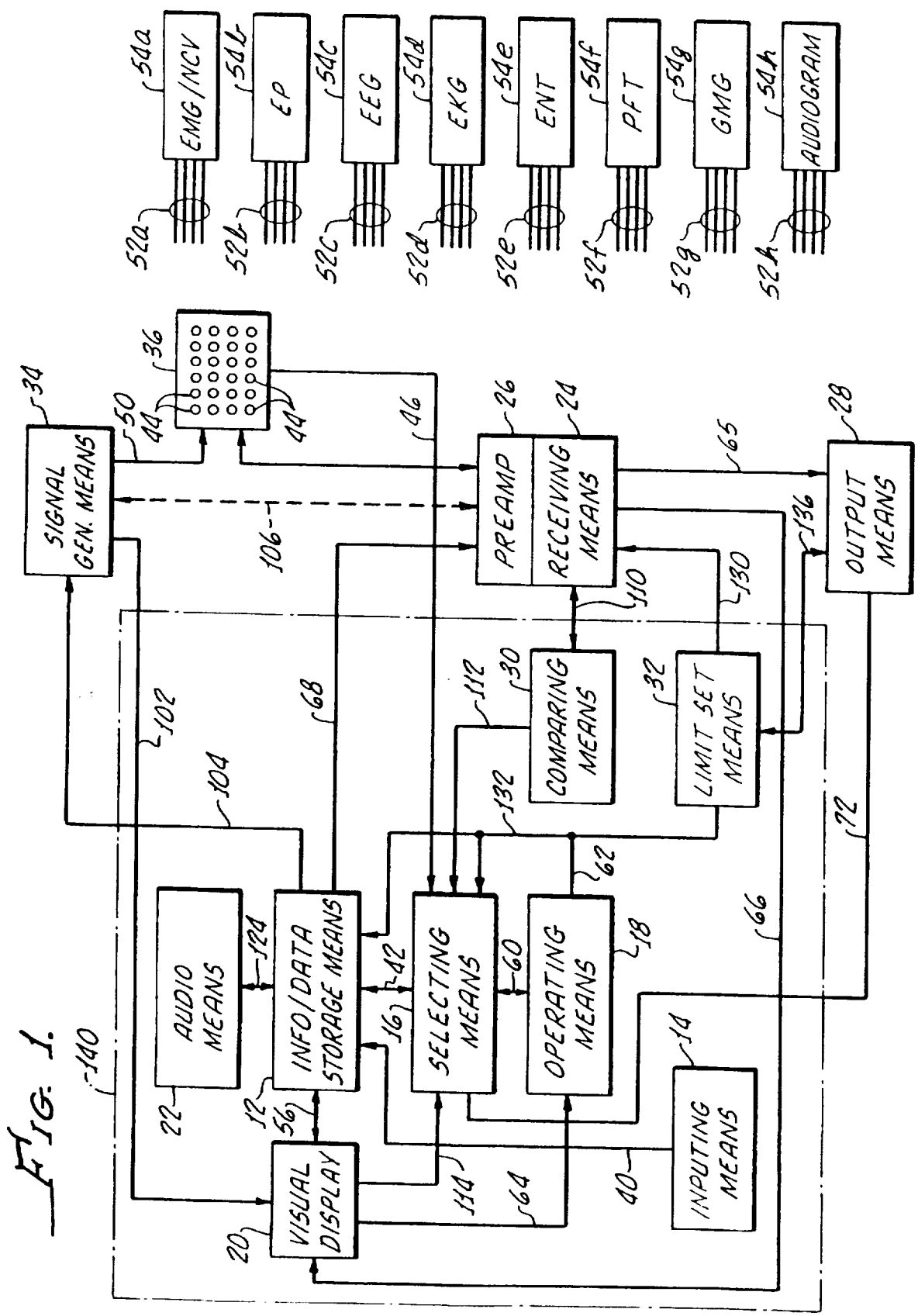
FIG. 1 is a drawing, in functional block diagram form, showing the arrangement of the virtual medical instrument (VMI) system in accordance with the present invention.

There is shown in the drawing, in functional block diagram form, a virtual medical office system 10 in accordance with a preferred embodiment of the present invention. As more particularly described below, functionally comprising virtual medical instrument system 10 are information/data storage means 12, information/data inputting means 14, protocol selecting means 16, operating means 18a visual display 20, audio means 22, signal receiving means 24 having associated therewith or forming a part thereof a preamplifier 26, output means 28, comparing means 30, limit setting means 32, signal generating means 34 and a universal interface 36, all of the foregoing being functionally interconnected as depicted in FIG. 1.

By way of example and not of limitation, information/ data storage means 12 may comprise data storage portions of a computer (such as a hard disc) and inputting means 14 may, in combination be implemented by both a computer diskette drive and a computer keyboard. Selecting means 16 may comprise a computer keyboard, mouse, or a touch screen. Operating means 18 may comprise computer and operating portions of a computer and visual display 20 may comprise a computer monitor which may have touch screen capabilities. Audio means 22 may comprise a computer sound card and speakers.

Information/data storage means 12 stores two or more, and preferably a number of, medical diagnostic test protocols for tests to be performed on patients. Such tests and test protocols, which are well known to those skilled in the medical diagnostic art, would typically include two or more, and preferably most or all, of the protocols for EMG/NCV, EP, EEG, EKG, ENG, PFT, CMG, visual acuity, visual field, limb dynometry, vital signs, sensory testing and audiogram testing, are shown below in TABLE I.

As indicated in Table I, many of the listed diagnostic test protocols have several sub-routines. Table II provides a glossary of abbreviations used in Table I.

TABLE I

MEDICAL DIAGNOSTIC TESTS

| | | |
|---|---|---|
| EMG/NVC: | EMG: | EMG Fibs |
| | | EMG MUPs |
| | | SFEMG |
| | | MUP Analysis |
| | | EMG Power Spectrum |
| | NVC: | Motor NVC |
| | | Sensory NVC |
| | | F/H Wave |
| | | RNS |
| | | Blink Reflex |
| | | SSR |
| EP: | SSEP: | SSEP Upper Extremity |
| | | SSEP Lower Extremity |
| | VEP: | PRVEP |
| | | Flash VEP |
| | | ERG |
| | BAEP: | BAEP |
| EEG: | | Routine EEG |
| | | Brain Death Routine |
| | | Long Term Monitoring |
| | | Sleep Studies |
| EKG: | | 12 Lead EKG |
| | | r-r Interval Variability |
| ENG: | Pursuit: | Sine Wave |
| | | Sawtooth Wave |
| | | Square Wave |
| | Saccade: | Horizontal |
| | | Vertical |
| | | Narrow/Wide |
| | OKN: | Horizontal |
| | | Vertical |
| | | Right/Left |
| | Caloric Test: | Right/Left |
| | | Warm/Cold |
| AUDIOGRAM: | | Routine Audiometry |
| | | Speech Discrimination |
| | | Right/Left |
| PFT: | Flow/Time: | FVC/FEV1, FEV1/FVC |
| | | FEF 25-75 PEF |
| | | FET |
| | Pressures: | MIP |
| | | MEP |
| | | Compliance |
| | Flow/Vol: | Flow-Vol. Curve |
| CMG: | | Urethral Flow Rate |
| | | Sphincter ECG |
| | | Bladder Pressure |
| | | Urethral Pressure |
| | | Abdominal Pressure |
| | | Volumes |
| VISUAL ACUITY | | 20 foot Std. Snellen Chart |
| | | 14 Inch Reading Acuity |
| VISUAL FIELDS | | Small/Med./Large Target |
| | | Red/Green/Yellow Field |
| LIMB DYNAMOMETRY | | Grip Dynamometry |
| | | Pinch Dynamometry |
| | | Joint Dynamometry |
| VITAL SIGNS | | Automated Blood Pressure |
| | | Pulse Monitor |
| | | Ear Temp. Probe |
| SENSORY TESTING | | Vibratometry |
| | | Thermal |

TABLE II

DEFINITION OF ABBREVIATIONS

| | |
|---|---|
| EMG | Electromyogram |
| NCV | Nerve Conduction Velocity |
| SFEMG | Single Fiber EMG |
| EMG Fibs | EMG fibrillations |
| EMG Mups | EMG Motor Unit Potential |
| RNS | Repetitive Nerve Stimulation |
| SSR | Sympathetic Skin Response |
| EP | Evoked Potential |
| SSEP | Somatosensory Evoked Potential |
| VEP | Visual Evoked Potential |
| PRVEP | Pattern Reversal VEP |
| ERG | Electroretinogram |
| BAEP | Brain Stem Auditory EP |
| EEG | Electroencephalogram |
| EKG | Electrocardiogram |
| ENG | Eletronystagmography |
| OKN | Opticokinetic Nystasgmus |
| PFT | Pulmonary Function Testing |
| FVC | Forced Vital Capacity |
| FEV | Forced Expiatory Volume in 1 Sec. |
| FEV1/FVC | Ratio or Percentage Out in 1 Sec. |
| FEF 25-75 | Forced Expiratory Flow Rate |
| PEF | Peak Expiratory Flow |
| FET | Forced Expiratory Time |
| MIP | Maximum Inspiratory Pressure |
| MEP | Maximum Expiratory Pressure |
| CMG | Cystometrogram |

The diagnostic test protocols enabled by system 10 are input into information/data storing means 12 by inputting means 14, which is shown functionally connected to the storage means by a communication link 40. Inputting means 16 may also advantageously be used to input to storage means 12 patient information, such as patients' names, addresses, telephone numbers, medical history, insurance coverage, billing information and the physicians' analysis or diagnosis of patients' conditions based upon results of medical diagnostic tests performed on the patients by the use of system 10.

A principal function of selecting means 14, which is shown functionally connected to storage means 12 by a communication link 42, is to select any desired one of the stored diagnostic test protocols (including any sub-routines thereof) to be performed on a patient. Each diagnostic test protocol may advantageously be displayed on visual display 20 in the form of a "pull-down" menu from which the various sub-routines can be selected, for example by highlighting.

Universal interface 36, which functions as the interface between main portions of system 10 and the "outside world," is formed having a number, for example, about twenty-four (as shown in FIG. 1), of electrical contacts 44 which may be of the conventional plug-in type. Interface 36 is shown functionally connected to selecting means 16 by a communication link 46 and to preamplifier 26 and signal generating means 34 by respective communication links 48 and 50. Electrical contacts 44 of universal interface 36 are configured for accepting connection ends of individual conventional electrical wires or conduits 52 which form conduit sets 52a through 52h which are, in turn, used for performing the corresponding medical diagnostic tests which are programmed into storage means 12. Such tests are represented by reference numbers 54a through 54h for diagnostic tests EMG/NCV, EP, EEG, EKG, ENG, PFT, CMG and Audiogram tests, the protocols of which are assumed, for purposes of explaining the present invention, to be stored in information/data storage means 12.

When a user of system 10 selects, by selecting means 16, any desired one of the medical diagnostic test protocols (corresponding to any of tests 54a-54h) stored in storage means 12 to be run on a patient, a corresponding conduit set 52a-52h is connected (by the user or an assistant) to interface contacts 44 in a preestablished pattern. The conduit connection pattern associated with the particular medical diagnostic test protocol selected by the user of system 10 is preferably shown on visual display 20, which is functionally connected to storage means 12 by a communication link 56.

By way of illustrative example, with no limitations intended or implied, and referring to FIG. 1, if a user of system 10 selects the EKG test (54d) protocol to be performed on a patient, conduit set 52d would be connected to contacts 44 of universal interface 36 in accordance with a connection pattern shown on display 20. In this example, the patient ends of conduit set 52d would, of course, be connected in the appropriate manner to the patent on which the EKG test is to be performed.

Conduit sets 52a through 52h may be preexisting, for example, in the case of retrofitting a medical office or facility with virtual medical instrument system 10, or may be provided as part of the virtual medical instrument system, for example, in new office or facility installations. It is to be appreciated that although conduit sets 52a through 52h are shown as being different sets of conduits for descriptive purposes, more than one test may use a common set of conduits.

The appropriate one of conduit sets 52a–52h corresponding to the selected medical diagnostic test protocol is connected to universal interface 36 and the patient. Performing of the test is controlled by operating means 18 which is functionally connected to the selecting means 16 by a communication link 60, to storage means by a communication link 62 and to visual display 20 by a communication link 64.

During the performing of the selected medical diagnostic test on a patient, electrical signals are transmitted from the patient over the particular set of conduits (in the foregoing example of an EKG test, over conduit set 52d) to universal interface 36 and over communication link 48 to preamplifier 26 of receiving means 24. Preamplifier 26 appropriately amplifies the received signals from the patient undergoing the test as required by the selected diagnostic test protocol and the configuration of system 10.

The patient's electrical signals are transmitted from receiving means 24, over a communication link 64, to output means 28. The received patient signals are also transmitted from receiving means 24, over a communication link 66, to visual display 20 and over a communication link 68 to storage means 12. As shown on FIG. 1, visual display 20 is connected to storage means 12 by communication link 56.

Figure 2:
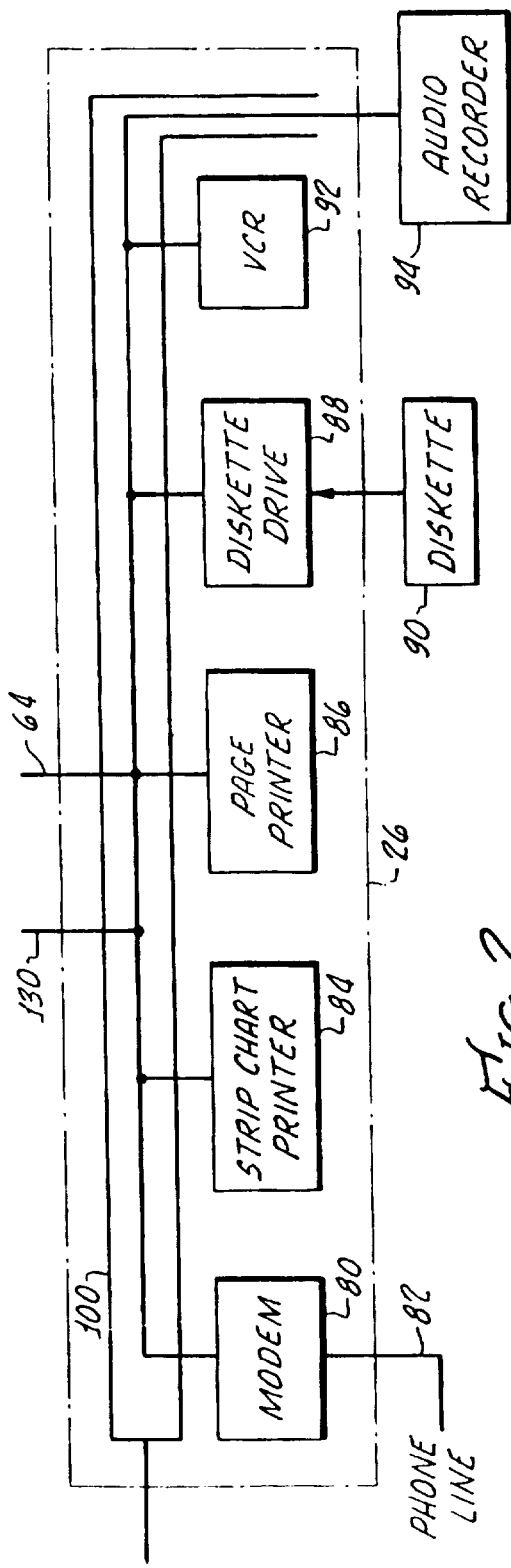
FIG. 2 is a drawing, in functional block diagram form, showing an output portion or means of the virtual medical instrument system of FIG. 1.

Without any intended or implied limitation, output means 28, as depicted in FIG. 2, preferably comprises one or more of a modem 80, to which is shown connected a telephone link 82; a strip chart printer 84, such is commonly used for the printing of continuous EKG signals from a patient; a conventional page or sheet printer 86; a diskette drive 88 which receives a conventional computer diskette 90; a video recorder 92; and an audio recorder 94.

Selecting means 16 is connected by communication link 72 to a switching bank 100 for selecting which one or ones of modem 80, strip chart printer 84, sheet printer 86, diskette drive 88, video recorder 92 and audio recorder 94 are connected for receiving and transmitting and/or recording the received patient signals associated with the selected medical diagnostic test being conducted.

Some stored medical diagnostic test protocols, for example, NCV and SSEP, require electrical stimuli to be applied to the patient on whom the test is being performed. The electrical signals received from the patient are in response to these stimuli signals applied to the patient.

Signal generator 34 is provided for the purpose of supplying such stimuli signals to the patient through communication link 50 to interface 36, and from there to the patient through the appropriately connected conduit set 52a–52h (FIG. 1). For visual monitoring purposes, the generated stimuli signals are provided from signal generating means 34 over communication link 102 to visual display 20. Communication between signal generating means 34 and storage means 12 is over a communication link 104.

In the event that the stimuli signals from signal generating means 34 require amplification, the signal generating means may be connected to preamplifier 26 by a communication link 106 (shown in dashed lines).

Preferably, system 10 includes provisions for determining whether the correct one of conduits sets 52a–52h (as determined by the selected diagnostic test protocol) is correctly connected to interface 36 and the selected medical diagnostic test is being correctly conducted on the patient on which the test is to be conducted. This may be accomplished by signal comparing means 30 which is connected to receiving means by a communication link 110 and to selecting means 16 by a communication link 112. Selecting means 16 is, as mentioned above, connected to storage means by a communication link 42 and to operating means 18 by a communication link 60; the selecting means are also connected to visual display 20 by a communication link 114. Consequently, comparing means 30 is connected to storage means 12, operating means 18 and visual display 20 through selecting means 16.

Figure 3B:
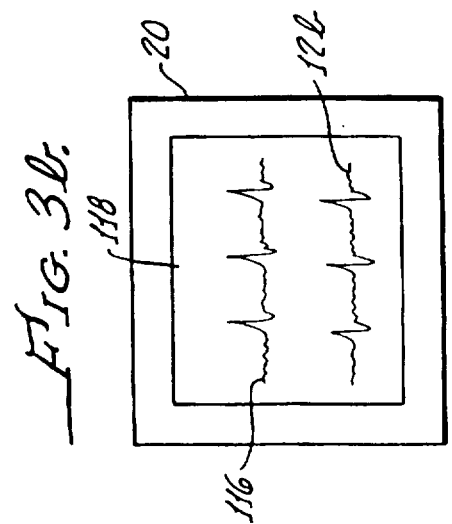
FIG. 3B showing the same exemplary electrical signal expected to be received from the patient and an actual received electrical signal that matches the expected signal, thereby indication no system error.
Figure 3A:
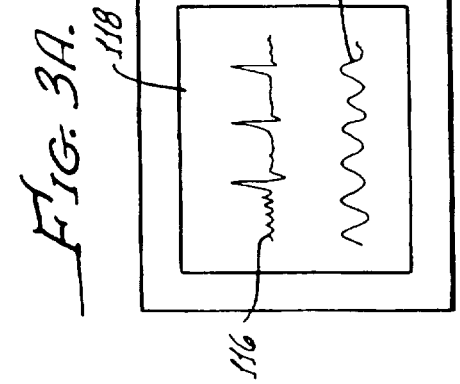
FIG. 3A showing an electrical signal that is expected to be received from the patient undergoing the selected diagnostic test and an actual received electrical signal that does not match the expected signal, thereby indicating a system error.

When a selected diagnostic test is initiated on a patient, according to the diagnostic test protocol selected, an electric signal that is expected to be received from the patient undergoing test is provided from storage means 12, through selecting means 16 and over communication links 42 and 112, to comparing means 30. Preferably, the expected signal is also displayed for visual monitoring by a user of system 10 as a trace 116 in upper regions of a display screen 118 of visual display 20, as depicted in FIGS. 3A and 3B.

The patient-generated electrical signals received by receiving means 24, through the appropriate conduit set (for example, set 52d), and communication link 48 from interface 36, is provided to comparing means 30 (via communication link 110) wherein it is compared with the expected signal from the patient for the diagnostic test being performed on the patient.

Preferably, the received patient signal is also provided to visual display 20 (through selecting means 16 and communication links 112 and 114) where it is displayed, for visual monitoring purposes, as a trace on screen 118. By way of illustrative example, there is depicted in FIG. 3A a patient signal trace 120a which does not correspond to signal trace 116 of the signal expected to be received from the patient undergoing the selected diagnostic test. This lack of correspondence indicates that the there is some testing problem or error. For example, the individual conduits of the conduit set that is used for the selected test may be incorrectly connected to contacts 44 of interface 36 or may be incorrectly connected to the patient. As another example, a set of conduits for a diagnostic test other than the selected diagnostic test may inadvertently have been connected to interface 36.

Comparing means 30 are operative for electronically comparing the expected and actual electrical signals from the patient. In the situation just discussed above wherein the actual signals received from the patient do not correctly correspond, with the expected signals, comparing means 30 instruct operating means 18 (through selecting means 16 and communication links 112 and 60) to stop the test so that whatever problem that exist's can be corrected. An audio signal may also be provided by audio means 22 (which is connected to storage means 12 by a communication link 124) to alert the user of system 10 that an error or problem has occurred.

On the other hand, if the actual patient signal corresponds to the expected signal, as depicted in FIG. 3B for patient signal trace 120b, comparing means 30 will not detect any lack of correspondence between the expected and actual signals and the selected diagnostic test protocol will continued uninterruptedly.

It will be understood that system 10 can further be configured so that comparisons between expected patient signals and actual patient signals can be made at different phases of the selected diagnostic test protocol, as may, for example, be advantageous when electrical connections to the patient are changed during the test when or different stimuli signals are provided to the patient.

It is further preferred to enable a user of system 10 to set or select patient signal limits associated with the selected medical diagnostic test protocol so that the user is, for example, alerted to possible patient medical problems indicated by the received patient electrical signals. To this end, limit setting means 32 are connected to receiving means 24 by communication link 130 and to selecting means 16 by a communication link 132 (FIG. 1). As in the case of above-described comparing means 30, limit setting means 32 are also connected for providing a visual display of the set limits to visual display 20 through communication link 114 from selecting means 16.

Figure 4:
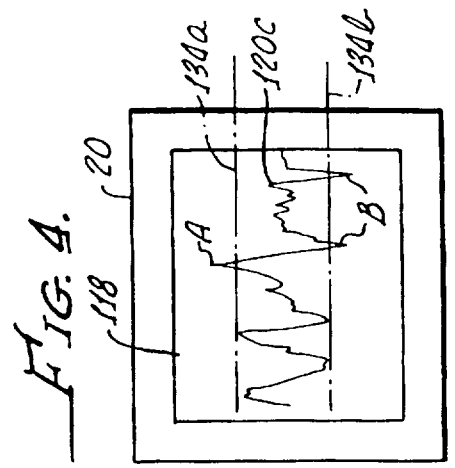
FIG. 4 is a representative diagram depicting the selection of maximum and minimum limits applied to an electric signal received from a patient undergoing a selected medical diagnostic test.

By way of illustrative example, there is depicted in FIG. 4 a received patient signal represented by signal trace 120c on screen 118 of visual display 20. Also depicted are a horizontal user-set upper limit trace 134a and a horizontal lower limit trace 134b (shown by broken lines). In this example, it can be seen in FIG. 4 that patient signal trace 120c exceeds upper limit trace 134a at one point "A" and exceeds (i.e., is below lower limit trace 134b) at two points "B".

In the case of user-set limits, it is desirable for traces 134a and 134b to be preset so as to automatically change or vary according to the ranges of expected patient signals during different phases of the selected diagnostic test protocol.

The printing, storing and/or communicating of the received patient signals associated with the selected diagnostic test protocol is enabled by output means 28, which as above-described may advantageously comprise a several different media, such as strip chart printer 84, page printer 86, diskette drive 88, VCR 93, audio recorder 94 and modem 80 (FIG. 2). As an illustration, by selecting means 16, which is connected to output means 28 by communication link 72, a patient's EKG signal may simultaneously be printed out in real-time on strip chart recorder 84, be stored for future analysis or permanent record by VCR 92 and transmitted to another location vis modem 80.

Limit setting means 32 may be connected to output means 28 by a communication link 136 so that the selected limits can be output along with the patient signals. Accompanying the patient signals from output means 28 may be such related patient information as name, address, prior test results, diagnoses, prescriptions, medical insurance carrier and limits, and test protocol information, such as date of test, attending physician, and comments regarding the test, as may be provided from storage means 12 (through selecting means 16 and communication links 42 and 72).

Medical instrument system 10 has been depicted in FIGS. 1-4 and has been described above in a functional manner. That is, major functions of system 10 have been shown as separate functional blocks in and are shown interconnected with a number of communication links, such as link 42 between storage means 12 and selecting means 42. All communication links are depicted in FIG. 1 as two way communication links (by showing arrows at both ends of the links) as will ordinarily be utilized. The illustrated communication links may comprise discrete wires or sets of wires or may comprise metalized paths between those functions that are constructed on a single chip or circuit board or card (not shown).

As indicated in the foregoing paragraph, virtual medical instrument system 10 may be implemented in a number of ways. It is presently preferred that storage means 12, selecting means 16, operating means 18, inputting means 12, visual display means 20, audio means 22, comparing means 30 and limit setting means 32 may be advantageously be formed as a computer work station 140, as shown in phantom lines in FIG. 1. Alternatively, system 10 may be constructed from discrete functional circuit boxes with two or several of the functions described above and depicted in FIG. 1 combined as multi-function circuits.

Although there has been described and illustrated a virtual medical instrument system and parts thereof in accordance with the present invention for purposes of illustrating the manner in which the invention may be used to advantage, it is to be appreciated that the invention is not limited thereto. Therefore, any and all variations and modifications that may occur to those skilled in the medical art are to be considered as being within the scope and spirit of the claims as appended hereto.

What is claimed is:

1. A virtual medical instrument system for a medical facility having a plurality of patient medical diagnostic test protocols, said virtual medical instrument comprising:

a. a universal interface having a number of electrical contacts, said universal interface being configured for having connected to at least some of said contacts any selected set of a plurality of different sets of electrical conduits associated with a like plurality of different patient diagnostic test protocols;

b. computer means for electronically storing said plurality of different patient diagnostic test protocols;

c. selecting means connected to said computer means for enabling the selection of any one of said plurality of different patient diagnostic test protocols for conducting on a patient, the simultaneous selection of the corresponding set of electrical conduits to be connected to particular electrical contacts of said universal interface, and for causing the selected diagnostic test protocol to be performed on said patient after the corresponding set of electrical conduits have been connected to the universal interface contacts and to the patient on which the selected diagnostic test protocol is to be performed;

d. receiving means connected to said universal interface for receiving electrical signals from the set of electrical conduits connected to said universal interface contacts from a patient undergoing said selected diagnostic test protocol and for providing said electrical signals to said computer means; and e. output means connected to said computer means for providing a detectable output corresponding to said received electrical signals.

2. A virtual medical instrument system for a medical facility having a plurality of patient medical diagnostic test protocols, said virtual medical instrument comprising:
   a. a universal interface having a number of electrical contacts, said universal interface being configured for having connected to at least some of said contacts any selected set of a plurality of different sets of electrical conduits associated with a like plurality of different patient diagnostic test protocols;
   b. selecting means connected to information and data storage means for enabling a user of the system to select from said information and storage means any desired one of said plurality of different patient diagnostic test protocols for conducting on a patient, and for selecting the appropriate set of electrical conduits to be connected to corresponding electrical contacts of said universal interface;
   c. operating means for causing the selected diagnostic test protocol to be performed on said patient after said appropriate electrical conduits are connected between said corresponding electrical contacts of said universal interface and said patient on which the selected diagnostic test protocol is to be performed;
   d. receiving means connected to said universal interface for receiving electrical signals from the set of electrical conduits connected to said universal interface contacts from a patient undergoing said selected diagnostic test protocol, said receiving means including a preamplifier connected to said universal interface for amplifying one or more of the electrical signals received therefrom; and
   e. output means for providing a detectable output corresponding to said received electrical signals.

3. A virtual medical instrument system for a medical facility having a plurality of patient medical diagnostic test protocols, said virtual medical instrument comprising:
   a. a universal interface having a number of electrical contacts, said universal interface being configured for having connected to at least some of said contacts any selected set of a plurality of different sets of electrical conduits associated with a like plurality of different patient diagnostic test protocols;
   b. selecting means connected to information and data storage means for enabling a user of the system to select from said information and storage means any desired one of said plurality of different patient diagnostic test protocols for conducting on a patient, and for selecting the appropriate set of electrical conduits to be connected to corresponding electrical contacts of said universal interface, said selecting means including verifying means for assuring that when the electrical contacts associated with the selected diagnostic test protocol are connected to particular ones of the universal interface contacts only the preselected diagnostic test protocol is enabled;
   c. operating means for causing the selected diagnostic test protocol to be performed on said patient after said appropriate electrical conduits are connected between said corresponding electrical contacts of said universal interface and patient on which the selected diagnostic test protocol is to be performed;
   d. receiving means connected to said universal interface for receiving electrical signals from the set of electrical conduits connected to said universal interface contacts from a patient undergoing said selected diagnostic test protocol; and
   e. output means for providing a detectable output corresponding to said received electrical signals.

* * * * *